United States Patent [19]

Heaulme et al.

[11] Patent Number: 5,292,745
[45] Date of Patent: Mar. 8, 1994

[54] USE OF 4-(3-TRIFLUOROMETHYLPHENYL)-1,2,3,6-TETRAHYDROPYRIDINE DERIVATIVES AS FREE RADICAL SCAVENGERS

[75] Inventors: Michel Heaulme, Montpellier, France; Umberto Guzzi, Milan, Italy

[73] Assignee: Elf Sanofi, Paris, France

[21] Appl. No.: 830,857

[22] Filed: Feb. 4, 1992

[30] Foreign Application Priority Data

Feb. 5, 1991 [FR] France .................. 91 01283

[51] Int. Cl.$^5$ .................. C07D 211/70; A61K 31/44; A61K 31/445
[52] U.S. Cl. .................. 514/277; 546/340; 546/346
[58] Field of Search .................. 546/340, 346; 514/277

[56] References Cited

U.S. PATENT DOCUMENTS

| 4,472,408 | 9/1984 | Nisato et al. | 514/277 |
| 4,521,428 | 6/1985 | Nisato et al. | 514/277 |
| 4,602,024 | 7/1986 | Nisato et al. | 514/357 |
| 4,691,019 | 9/1987 | Nisato et al. | 546/330 |
| 5,009,005 | 4/1991 | Bieganski | 30/90.6 |
| 5,026,716 | 6/1991 | Bianchetti et al. | 514/336 |
| 5,109,005 | 4/1992 | Croci et al. | 514/277 |

OTHER PUBLICATIONS

Woodruff et al., *Annals of the Rheumatic Diseases*, 45, 1986, 608–611.
Cross et al., *Annals of Internal Medicine*, 107, 4, 1987, 526–545.

Primary Examiner—Alan L. Rotman
Attorney, Agent, or Firm—Bacon & Thomas

[57] ABSTRACT

The invention concerns the use of a compound of formula (I)

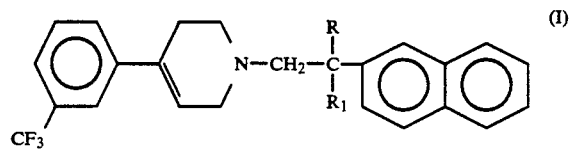

wherein R and $R_1$, each independently, represent a hydrogen atom or a methyl group, and its pharmaceutically acceptable acid addition salts, as free radical scavengers. The pharmaceutical compositions containing these compounds may be employed in the treatment and/or prevention of pathological processes involving cell damage due to the formation of free radicals.

The invention also concerns the compounds of formula (I) wherein at least one of R and $R_1$ is methyl, which are new compounds, as well as the process for the preparation thereof and the pharmaceutical compositions containing them.

1 Claim, No Drawings

USE OF 4-(3-TRIFLUOROMETHYLPHENYL)-1,2,3,6-TETRAHYDROPYRIDINE DERIVATIVES AS FREE RADICAL SCAVENGERS

The present invention refers to a new therapeutic use of some tetrahydropyridine derivatives as well as to the new compounds thus employed.

European patent application EP-A-101,381 discloses a class of tetrahydropyridine derivatives of general formula (A)

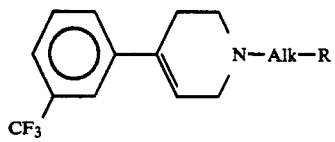

wherein Alk represents a straight or branched alkylene chain of from 2 to 4 carbon atoms and R is pyridyle, pyridyle N-oxide, unsubstituted naphthyl or naphthyl substituted with a lower alkyl group.

For the compounds of this class an anorexigenic activity has been indicated and claimed in the above patent application.

Another European patent application, EP-A-369,887, describes the use of some compounds of formula (A) wherein R is inter alia a naphthyl group, as therapeutic agents for treating anxiety and anxio-depressive disorders.

It has now been found that the compounds of formula (A) above, wherein R is a 2-naphthyl group and Alk stands for an ethylene group optionally substituted with one or two methyl groups on the carbon atom linked to the R group, as well as their acid addition salts are endowed with very interesting pharmacological properties as free radical scavengers.

A first specific object of the present invention is therefore the use of at least one compound of formula (I)

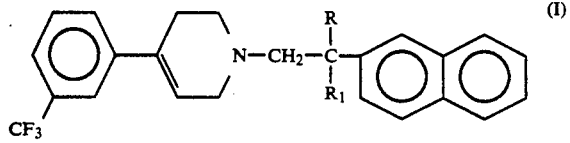

wherein R and $R_1$, each independently, may represent a hydrogen atom or a methyl group, or one of its pharmaceutically acceptable acid addition salts, for the preparation of a medicament for the treatment or prevention of those clinical conditions in which free radicals are implicated.

Free radicals are chemical species containing one or more unpaired electrons which being highly reactive may start uncontrollable chain reactions at cell level.

They are capable therefore of reversibly or unreversibly damaging compounds of all biochemical classes including proteins, amino acids, lipids, lipoproteins, nucleic acids, and carbonhydrates thus affecting such cell main activities as membrane function, metabolism, and gene expression.

There are many clinical disorders wherein an important role of free radicals, either as primary or secondary etiological agents or as amplifiers of the original disease, has been envisaged (see Oxygen Radicals and Human Disease—*Annals of Internal Medicine*, 1987, 107, 526–545 and more particularly the Table on page 527 which is incorporated within the present application by reference).

Substantial evidence has recently been produced to confirm the role of free radicals in post-injury degeneration of the brain and spinal cord and in ischemic-reperfusion injury (B. Halliwell Ed., Proceedings of the Upjohn Symposium on Oxidants and *Disease—Bethesda: Federation of American Societies for Experimental Biology*, 1987, and J. M. McCord, *N.Eng.J.Med.*, 1985, 312, 159–163).

It seems to be certain in fact that in ischemias the lesions due to the hypoxia are less damaging than those caused by the large flux in the ischemic tissues of oxygen derived free radicals that occurs when blood circulation is restored.

It has also been demonstrated that the lesions which are caused by reperfusion are not limited to heart and brain but also affect kidney, liver, pancreas, and the endothelial vascular and smooth muscle system.

Particularly apparent is the role of oxygen radicals in myocardial injury caused by ischemia-reperfusion (S. R. Jolly et al., *Circ. Res.*, 1984, 54, 227–85; L. C. Becker et al., *Prog.Cardiovasc.Dis.*, 1987, 30, 23–44; and R. Bolli et al., *Circ.Res.*, 1989, 65, 607–622).

It has also been demonstrated that injury by free radicals may also occur in inflamed rheumatoid joints (T. Woodruff et al., *Am.Rheum.Dis.*, 1986, 45, 608–611).

In general the compounds of formula (I) may be employed in therapy in any pathological process which involves cellular damage as it has been shown that in all these processes oxygen radicals are implicated.

More precisely, clinical indications where the compounds of formula (I) may suitably be used include therefore protection against post-injury degeneration of the brain and spinal cord, and ischemia-reperfusion injury.

Other clinical indications wherein the compounds of formula (I) and their pharmaceutically acceptable acid addition salts, as free radical scavengers, may be employed include protection against damage in the cornea and retina caused by oxygen radicals, such as cataract of oxydative origin and retinopathy of prematurity; organ preservation, particularly kidney preservation, for transplantations; protection against damage by radiation; prevention of relapse of duodenal ulcers; and protection against tissue damage by toxic agents whose toxicity is due to the production of free radicals.

For the use as free radical scavengers the compounds of formula (I) as well as their pharmaceutically acceptable salts may suitably be administered orally, sublingually, parenterally, transdermally or topically, formulated in pharmaceutical compositions.

Said pharmaceutical compositions contain at least one compound selected from the class consisting of the compounds of formula (I) and their pharmaceutically acceptable acid addition salts, in admixture with an inert pharmaceutical carrier.

Both organic and inorganic acids can be employed to form non-toxic pharmaceutically acceptable salts of the compounds of formula (I). Illustrative acids are sulfuric, nitric, phosphoric, hydrochloric, citric, acetic, lactic, tartaric, pamoic, ethanedisulfonic, sulfonic, succinic, cyclohexylsulfonic, fumaric, maleic, and benzoic acid.

As for the oral or sublingual administrations, optionally sugar-coated tablets, capsules, optionally sustainedrelease granules, drops, and liposomes, are preferably employed. As for the intravenous, subcutaneous, or intramuscular administration, sterile or sterilisable solutions are employed, particularly those suitable as intravenous infusions, while conventional patches may be used for transdermal administration. For topical administration, ointments or lotions to be applied to the skin, solutions or ophthalmic ointments for the eyes can be employed.

The pharmaceutical compositions according to the present invention may be prepared according to techniques and procedures well known in industrial pharmacy.

In the preparation of said pharmaceutical compositions the active principle may be incorporated in the ordinarily used excipients such as talc, arabic gum, lactose, starch, magnesium stearate, aqueous or non aqueous vehicles, fats of animal or vegetable origin, paraffin derivatives, glycols, various wetting, dispersing, or emulsifying agents, preservatives, etc.

The pharmaceutical compositions of the invention may advantageously contain a compound of formula (I) or one of its pharmaceutically acceptable salts in combination with one or more other known drugs generally employed for the same therapeutical indications.

The amount of active principle to be administered daily, according to the method of the present invention, depends on the particular therapeutical indication, the severity of the conditions to be treated as well as the weight of the patient and the administration route.

For systemic administration the overall daily dosage in humans is generally comprised between 2 and 900 mg, for instance between 3 and 500 mg, and more advantageously between 10 and 300 mg.

Unit dosage forms for systemic administration will typically contain from 2 to 300 mg, preferably from 5 to 150, comprising for instance from 5 to 50 mg (namely 5, 10, 20, 30, 40, and 50 mg) of active compound. Typically, said unit dosage forms will be administered once or more times a day, preferably on a regimen of 1-3 times a day.

For topical administration, the pharmaceutically compositions typically contain from 0.0001 to 1% of active principle and preferably from 0.001 to 0.5%. The unit dosage form for ophthalmic administration (a drop) will generally contain from 10 ng to 10 mg, and preferably from 100 ng to 1 mg of active principle.

A further specific object of the present invention is therefore a method to prevent and control pathological conditions implicating free radicals which method comprises administering to a subject in need thereof an effective amount of at least one compound of formula (I) or of a pharmaceutically acceptable salt thereof.

The compounds of formula (I) wherein one of R and $R_1$ is methyl and the other is a hydrogen atom or a methyl group as well as their acid addition salts are new compounds and represent a further specific object of the present invention.

The compound of formula (I) wherein one of R and $R_1$ is methyl and the other is hydrogen contains a chiral center. The present invention includes in its scope the pure isomers of this compound as well as any mixture thereof.

These compounds may be prepared, according to a general method, by a process which comprises the reduction of the corresponding amide of formula (II)

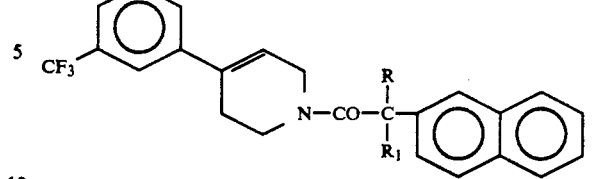

wherein one of the radical R and $R_1$ is methyl and the other is hydrogen or methyl.

Said reduction may advantageously be carried out by means of an aluminum hydride or a complex lithium aluminum hydride in an inert organic solvent at a temperature comprised between 0° C. and the reflux temperature of the reaction mixture. The thus obtained product may then be optionally converted into one of its acid addition salts.

The reduction reaction is carried out according to well known procedures by using, as the reducing agent, aluminum hydride or a complex lithium aluminum hydride, such as $LiAlH_4$, $LiAlH(OCH_3)_3$ and the like. Generally the reaction is carried out in an inert solvent such as an ether, e.g. diethyl ether, tetrahydrofuran, dioxane or 1,2-dimethoxyethane.

According to a preferred embodiment, the reaction is carried out using a double molar proportion of $LiAlH_4$ with respect to the starting compound of formula (II), at a temperature of 20°-30° C., in diethyl ether and under inert atmosphere. After about one hour, the reduction reaction is complete and the desired compound is isolated according to conventional techniques as the free base or as an acid addition salt thereof.

The free base may be converted into one of its salts by simple salification in an organic solvent such as an alcohol, preferably ethanol or isopropanol, an ether, such as 1,2-dimethoxyethane, ethyl acetate or a hydrocarbon such as hexane.

The above compounds of formula (II) are prepared by reacting 4-(3-trifluoromethylphenyl)-1,2,3,6-tetrahydropyridine of formula (III)

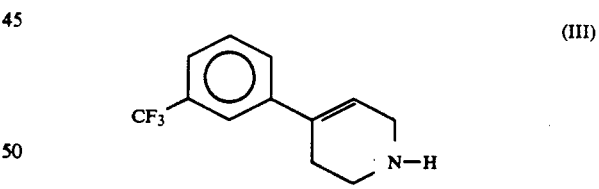

with a functional derivative of a carboxylic acid of formula (IV)

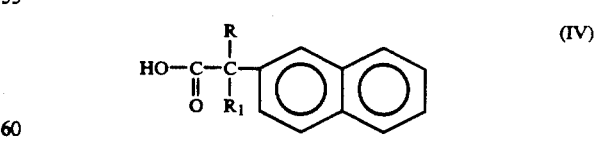

wherein one of R and $R_1$ is methyl and the other is hydrogen or methyl, in an organic solvent at a temperature comprised between —10° C. and the reflux temperature of the reaction mixture.

As suitable functional derivatives there may be cited the activated free acid (e.g. with BOP), the anhydride, mixed anhydrides, active esters and acid halides, preferably acid chlorides. Among the active esters, particularly preferred is the p-nitrophenyl ester, but methoxyphenyl, trytyl, benzhydryl and the like esters are also suitable.

The reaction temperature may range between −10° C. and the reflux temperature but generally the reaction is carried out at room temperature or at a temperature of 30°-50° C. It may be convenient to carry out the reaction in the cold when it is exothermic, e.g. when an acid chloride is employed as functional derivative of the acid of formula (IV).

As for the reaction solvent, preferably an alcohol is employed such as methanol or ethanol, or a halogenated solvent such as methylene chloride, dichloroethane, chloroform and the like solvents, but other organic solvents compatible with the reactants, such as dioxane, tetrahydrofuran, or hydrocarbons, e.g. hexane, may be employed as well.

The reaction may conveniently be carried out in the presence of a proton acceptor, such as an alkali metal carbonate or a tertiary amine.

The product obtained at the end of the reaction is generally an oil which may be isolated and characterised according to conventional techniques or employed as such in the subsequent reduction reaction.

Alternatively, the new compounds of formula (I) may be prepared by reacting 4-(3-trifluoromethylphenyl)-1,2,3,6-tetrahydropyridine of formula (III) with a compound of formula (V)

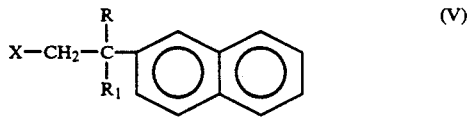

wherein one of R and R₁ is methyl and the other is hydrogen or methyl and X represents chloro, bromo, iodo or an electronwithdrawing group such as methanesulfonyloxy or p-toluenesulfonyloxy.

The reaction is carried out in an organic solvent at a temperature of from room temperature to 200° C.

Preferred organic solvents are aliphatic alcohols of 1 to 6 carbon atoms, such as methanol, ethanol, n-butanol, n-pentanol, but other organic solvents such as hexane, dimethylformamide, dimethylsulfoxide, sulfolane, acetonitrile, pyridine, and the like solvents may be employed as well.

The reaction is conveniently carried out in the presence of a basic condensation agent, such as triethylamine, particularly when X represents a halogen atom.

The reaction temperature may range between room temperature (about 20° C.) and 200° C. and the reaction time will depend on the temperature employed. In general, the reaction is complete after heating at 100°-150° C. for 4-5 hours and the thus obtained end product is then recovered according to conventional techniques and optionally converted into a salt thereof by simple salification in an organic solvent such as an alcohol, preferably ethanol or isopropanol, an ether, such as 1,2-dimethoxyethane, ethyl acetate or a hydrocarbon, such as hexane.

Furthermore, when a compound of formula (I) is desired wherein one of R and R₁ is methyl and the other is hydrogen, it may also be prepared by reacting 4-(3-trifluoromethylphenyl)-1,2,3,6-tetrahydropyridine (III) with the compound of formula (VI)

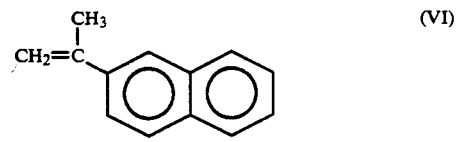

in the presence of a basic condensation agent.

PREPARATION I

1-[4-(3-trifluoromethylphenyl)-1,2,3,6-tetrahydropyrid-1-yl]-2-(naphth-2-yl)propane hydrochloride a) A solution of 2-(naphth-2-yl)propanoic acid ethyl ester (8 g, 0.035 mol) and potassium hydroxide (8 g) in a mixture of methanol (80 ml) and water (80 ml) is heated to 40° C. for 2 hours. The reaction mixture is then concentrated to dryness, the residue is dissolved in water (100 ml) and concentrated hydrochloric acid is added thereto to bring the pH to 3.5. The precipitate which forms is recovered by filtration and dissolved in ethyl ether and the thus obtained solution is filtered on celite and concentrated to dryness thus affording 2-(naphth-2-yl)propanoic acid (4.4 g). M.p. 112°-114° C.

b) A solution of the product obtained in step a) above (4.2 g, 0.021 mol) and 1,1-carbonyldiimidazole (3.5 g, 0.021 mol) in tetrahydrofuran (40 ml) is stirred at room temperature for 1 hour. A solution of 4-(3-trifluoromethylphenyl)-1,2,3,6-tetrahydropyridine (4 g, 0.021 mol) in tetrahydrofuran (20 ml) is then added thereto and the reaction mixture is stirred at room temperature for 2 hours and concentrated to dryness. The thus obtained residue is dissolved in ethyl ether and the solution is then washed with water, 2N HCl, water, 10% NaHCO₃, and finally with water. The washed solution is filtered on celite and concentrated to dryness thus affording an oily product (6.3 g) consisting of 1-[4-(3-trifluoromethylphenyl)-1,2,3,6-tetrahydropyrid-1-yl]-1-oxo-2-(naphth-2-yl)propane.

c) A solution of the compound obtained in step b) above (6.3 g, 0.015 mol) in ethyl ether (60 ml) is dripped into a suspension of LiAlH₄ (1.15 g, 0.031 mol) in ethyl ether (20 ml) and the reaction mixture is then stirred at room temperature for 2 hours. Excess reducing agent is then destroyed by the dropwise addition of water, the mixture is filtered and the filtrate is concentrated to dryness. The residue is dissolved in acetone and the compound of the title, as a raw product, is precipitated from the obtained solution by the addition of hydrogen chloride. The precipitate is recovered by filtration, the free base is obtained therefrom by neutralization with sodium hydroxide, extraction with ethyl acetate and evaporation of the organic solvent. The obtained product, as the free base, is then purified by flash chromatography eluting with cyclohexane/ethyl acetate 9/1, and converted into the corresponding hydrochloride by treatment with hydrogen chloride in propanol. The product is allowed to crystallise and is recovered by filtration affording the compound of the title (1.5 g). M.p. 178°-180° C.

PREPARATION II

1-[4-(3-trifluoromethylphenyl)-1,2,3,6-tetrahydropyrid-1-yl]-2-methyl-2-(naphth-2-yl)propane hydrochloride a) A solution of 2-methyl-2-(naphth-2-yl)propanoic acid ethyl ester (7 g, 0.028 mol) and potassium hydroxide (7 g) in a mixture of ethanol (40 ml) and water (40 ml) is heated to the reflux temperature for 2 hours. The reaction mixture is then concentrated to dryness, the residue is dissolved in water and the aqueous solution is washed with ethyl ether. Concentrated hydrochloric acid is added thereto to bring the pH to 1, the precipitate which forms is recovered by filtration and crystallised from ethanol 50° (40 ml) thus affording 2-methyl-2-(naphth-2-yl)propanoic acid (3 g). M.p. 125°–127° C.

b) A solution of the product obtained in step a) above (3 g, 0.014 mol), 4-(3-trifluoromethylphenyl)-1,2,3,6-tetrahydropyridine (3.6 g, 0.014 mol), benzotriazol-1-yloxytris(dimethylamino)phosphonium hexafluorophosphate (BOP) (5.6 g, 0.014 mol), and triethylamine (4 ml, 0.028 mol) in methylene chloride (40 ml) is allowed to stand at room temperature for 4 hours. The reaction mixture is then concentrated to dryness, the residue is taken up with ethyl acetate and the solution is then washed sequentially with water, 2N HCl, water, 2N NaOH, and water. The washed solution is filtered on celite and concentrated to dryness thus affording 1-[4-(3-trifluoromethylphenyl)-1,2,3,6-tetrahydropyrid-1-yl]-1-oxo-2-methyl-2-(naphth-2-yl)propane (4 g).

c) A solution of the compound obtained in step b) above (4 g, 0.0094 mol) in ethyl ether (40 ml) is dripped into a suspension of LiAlH$_4$ (0.7 g, 0.0184 mol) in ethyl ether (40 ml). The reaction mixture is then stirred at room temperature for 4 hours and excess reducing agent is then destroyed by the dropwise addition of water (1.5 g). The obtained residue is then purified by flash chromatography eluting with cyclohexane/ethyl acetate 15/1. The free base is thus obtained (1.4 g) which is then dissolved in isopropanol. Hydrochloric acid in ethanol is added thereto and the compound of the title is then allowed to crystallise yielding 1.2 g. M.p. 231°–233° C.

PHARMACOLOGICAL EVALUATION

The free radical scavenging properties of the compounds of formula (I) have been determined by means of a lipid peroxidation test carried out as described in the following:

rat brain homogenates (1.5 mg/ml) have been incubated in Krebs buffer (100 μl) (composed of 15 mM HEPES, pH 7.4, 10 mM glucose, 140 mM NaCl, 3.6 mM KCl, 1.5 mM CaCl$_2$, 1.4 mM KH$_2$PO$_4$, and 0.7 mM MgCl$_2$), at 37° C. for 20 minutes following the addition of 200 μM Fe$^{2+}$ to initiate the reactions. Lipid peroxidation has been assessed by the formation of thiobarbituric acid-reactive oxidation products (TBAR) during the 20 minute incubation as described by J. Braughler et al. in *J. Biol. Chem.*, 1986, 261, 10282–10289. By the addition of different concentrations of the compounds of formula (I) in Krebs buffer, the IC$_{50}$ of these compounds, i.e. the concentration of test compound which affords a 50% inhibition of lipid peroxidation over the controls, has been easily calculated.

In this test the compounds of formula (I) showed to be very active. In particular the compound of formula (I) wherein R and R$_1$ are both hydrogen, as the hydrochloride, is characterised by an IC$_{50}$ of approximately 1–2 μM.

The compounds described in Preparation I and Preparation II, which have almost the same activity level, have the advantage over the compound of formula (I) wherein R and R$_1$ are both hydrogen of a very limited serotoninergic activity (the compound of Preparation I) or of no serotoninergic activity (the compound of Preparation II).

What is claimed:

1. A method of scavenging free radicals in human and animal subjects comprising administering to said subjects an effective amount of a compound of formula (I)

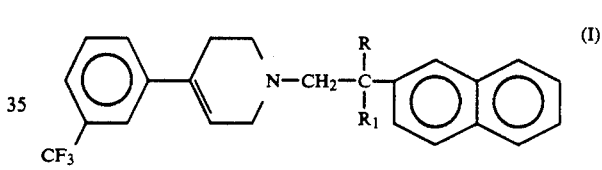

wherein R and R$_1$, each independently, represent a hydrogen atom or a methyl group, or of a pharmaceutically acceptable acid addition salt thereof.

* * * * *